US011471091B2

(12) United States Patent
Sivadas

(10) Patent No.: US 11,471,091 B2
(45) Date of Patent: Oct. 18, 2022

(54) MIND STRENGTH TRAINER

(76) Inventor: Kulangara Sivadas, Foothill Ranch, CA (US)

( * ) Notice: Subject to any disclaimer, the term of this patent is extended or adjusted under 35 U.S.C. 154(b) by 11 days.

(21) Appl. No.: 12/931,101

(22) Filed: Jan. 24, 2011

(65) Prior Publication Data

US 2012/0029379 A1    Feb. 2, 2012

Related U.S. Application Data

(60) Provisional application No. 61/400,554, filed on Jul. 29, 2010.

(51) Int. Cl.
| | |
|---|---|
| *A61B 5/375* | (2021.01) |
| *G06F 3/01* | (2006.01) |
| *A61B 5/00* | (2006.01) |
| *A61M 21/00* | (2006.01) |

(52) U.S. Cl.
CPC ............ *A61B 5/375* (2021.01); *A61B 5/7282* (2013.01); *A61M 21/00* (2013.01); *G06F 3/015* (2013.01); *A61M 2021/0016* (2013.01); *A61M 2021/0022* (2013.01); *A61M 2021/0027* (2013.01); *A61M 2021/0044* (2013.01); *A61M 2205/502* (2013.01); *A61M 2205/52* (2013.01); *A61M 2205/70* (2013.01); *A61M 2230/10* (2013.01); *A61M 2230/60* (2013.01); *A61M 2230/65* (2013.01)

(58) Field of Classification Search
CPC ..... A61B 5/165; A61B 5/0476; A61B 5/0482; A61B 5/375; A61B 5/7282; A61B 5/16–18; A61M 21/00; A61M 2021/0016; A61M 2021/0022; A61M 2021/0027; A61M 2021/0044; A61M 2205/502; A61M 2205/52; A61M 2205/70; A61M 2230/10; A61M 2230/60; A61M 2230/65; G06F 3/015
USPC ..................... 600/26–28, 300–301, 544–545
See application file for complete search history.

(56) References Cited

U.S. PATENT DOCUMENTS

| | | | | |
|---|---|---|---|---|
| 4,220,142 | A | * | 9/1980 | Rosen ........................ A61F 5/56 340/575 |
| 5,033,082 | A | * | 7/1991 | Eriksson .......... G10K 11/17881 379/406.08 |
| 5,311,877 | A | * | 5/1994 | Kishi ..................... G08B 21/06 340/575 |
| 5,377,100 | A | * | 12/1994 | Pope et al. .................... 600/545 |
| 5,724,987 | A | | 3/1998 | Gevins |
| 5,813,993 | A | | 9/1998 | Kaplan |
| 5,911,581 | A | | 6/1999 | Reynolds |
| 6,167,298 | A | * | 12/2000 | Levin ............................ 600/545 |

(Continued)

OTHER PUBLICATIONS

"Timer." https://en.wikipedia.org/wiki/Timer.*

(Continued)

*Primary Examiner* — Michael R Bloch

(57) ABSTRACT

An assortment of algorithms, procedures and associated device-hardware to condition human mind on causality between a specific state of mind and an externally generated stimuli, including a procedure to collect (310) bio signals underlying specific mental moods, characterize (330) them, monitor (350,360) bio signal activity to detect such moods, and play mind games that enhance mind's flexing power with the help of said device. Invention also includes a method (340) to evaluate and engineer mantras that serve as said externally generated stimuli.

6 Claims, 10 Drawing Sheets

First Embodiment of Mind Strength Trainer

(56) References Cited

U.S. PATENT DOCUMENTS

| | | | |
|---|---|---|---|
| 6,625,485 B2 | 9/2003 | Levendowski | |
| 2001/0031930 A1* | 10/2001 | Roizen et al. | 600/545 |
| 2003/0171688 A1* | 9/2003 | Yoo et al. | 600/544 |
| 2004/0138578 A1* | 7/2004 | Pineda et al. | 600/544 |
| 2007/0060831 A1* | 3/2007 | Le et al. | 600/544 |
| 2007/0173733 A1* | 7/2007 | Le et al. | 600/544 |
| 2008/0039737 A1* | 2/2008 | Breiter et al. | 600/544 |
| 2008/0319335 A1* | 12/2008 | Greene | A61B 5/4094 |
| | | | 600/544 |

OTHER PUBLICATIONS

An article titled 'Mindflex' from Wikipedia, the free encyclopedia (http://en.wikipedia.org/wiki/Mindflex), about a toy that uses EEG signals to effect motion of objects, published May 23, 2013.

An article titled 'Force Trainer' from Wikipedia, the free encyclopedia (http://en.wikipedia.org/wiki/Force_Trainer), about a toy that uses EEG signals to effect motion of objects, published Nov. 7, 2013.

An article titled 'Neurofeedback' from Wikipedia, the free encyclopedia (http://en.wikipedia.org/wiki/Neurofeedback), about technics such as alpha-theta training of mind, published Sep. 12, 2015.

\* cited by examiner

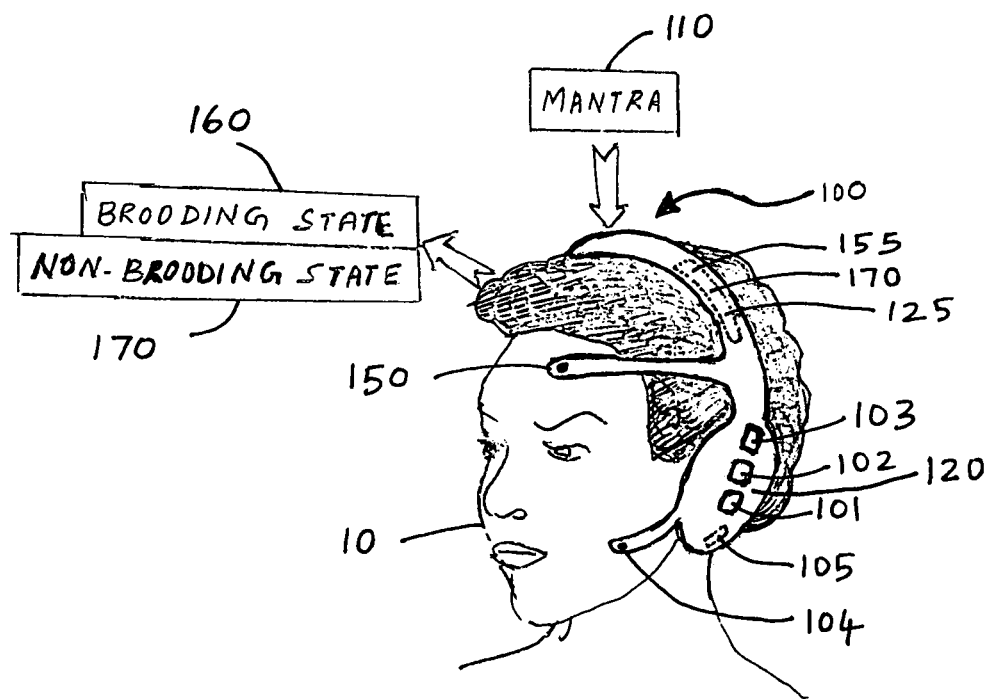
Fig.1- First Embodiment of Mind Strength Trainer

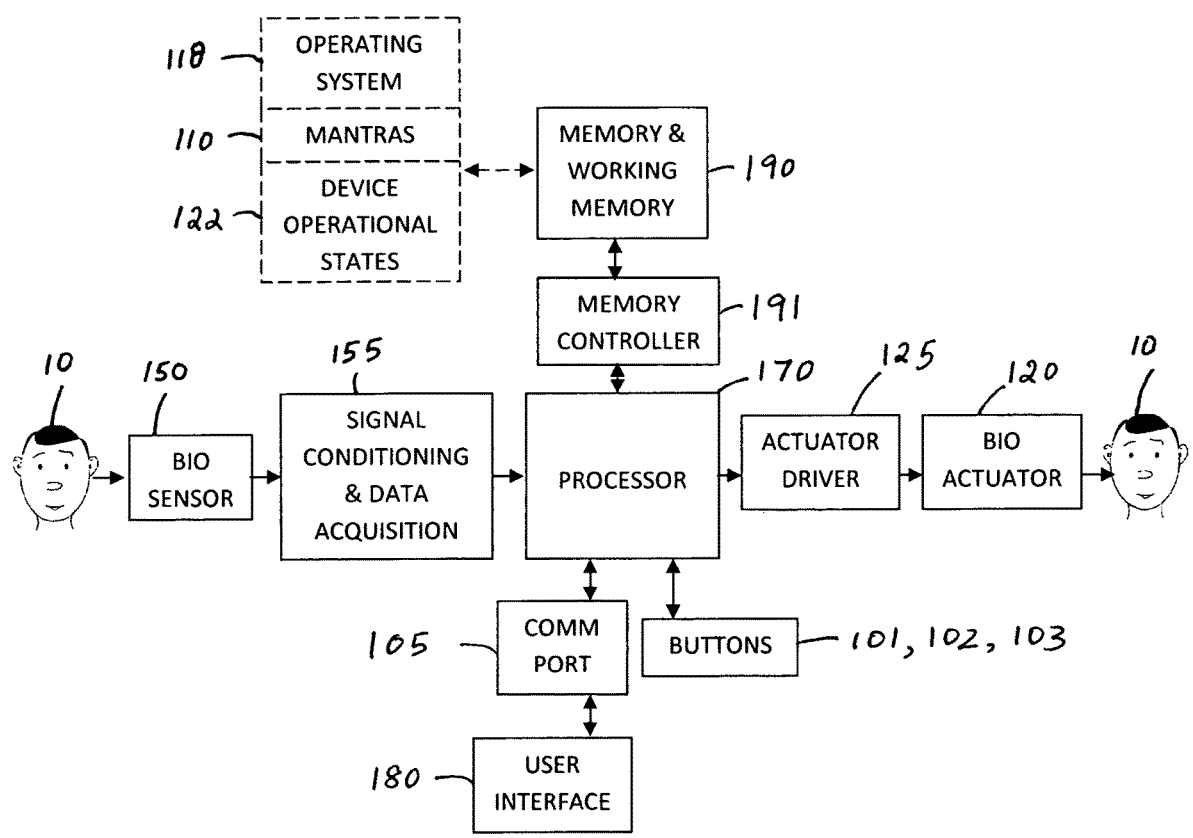
Fig.2- Electrical Schematics of Mind Strength Trainer

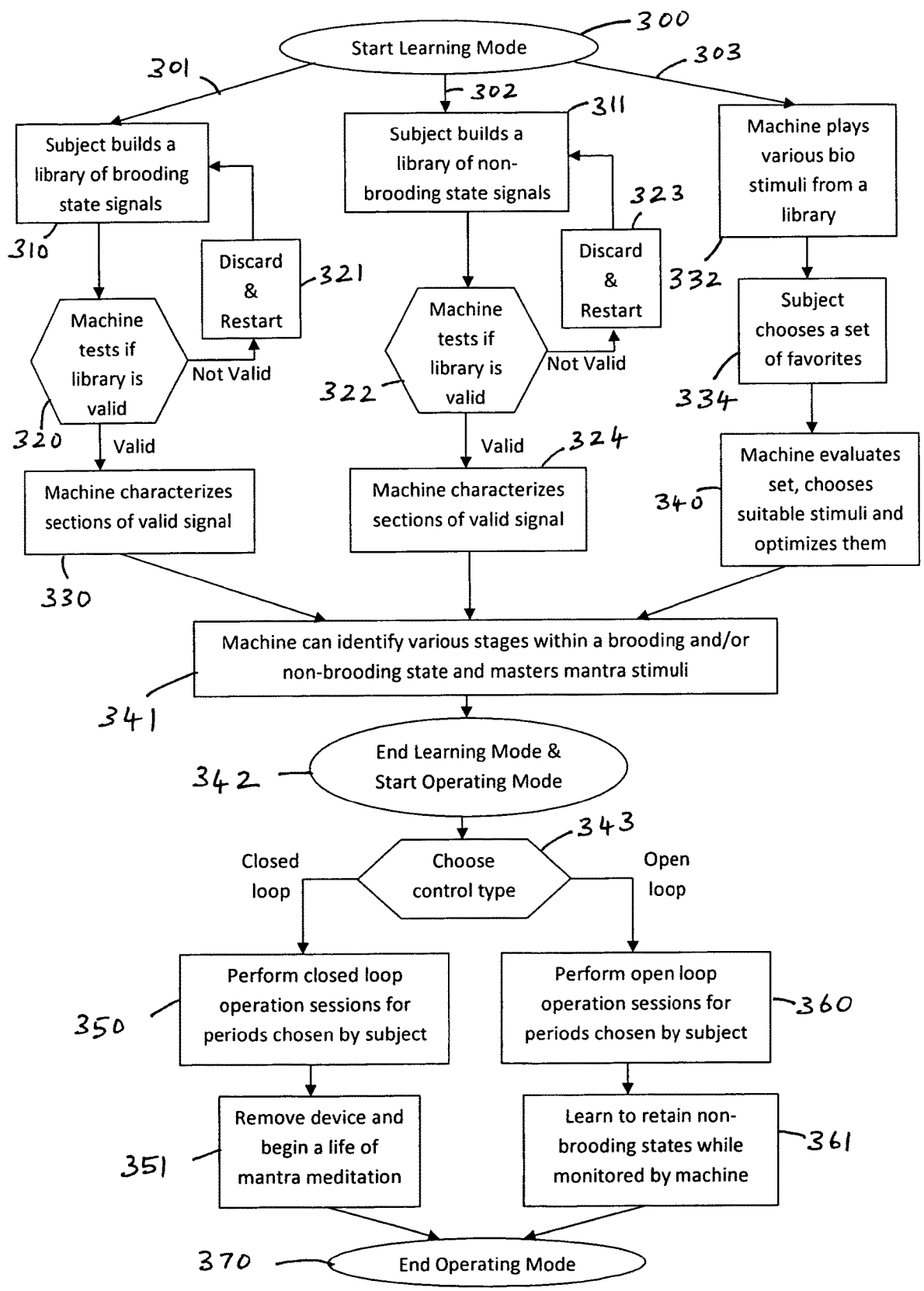
Fig.3- Top Level Flowchart of Device Operation

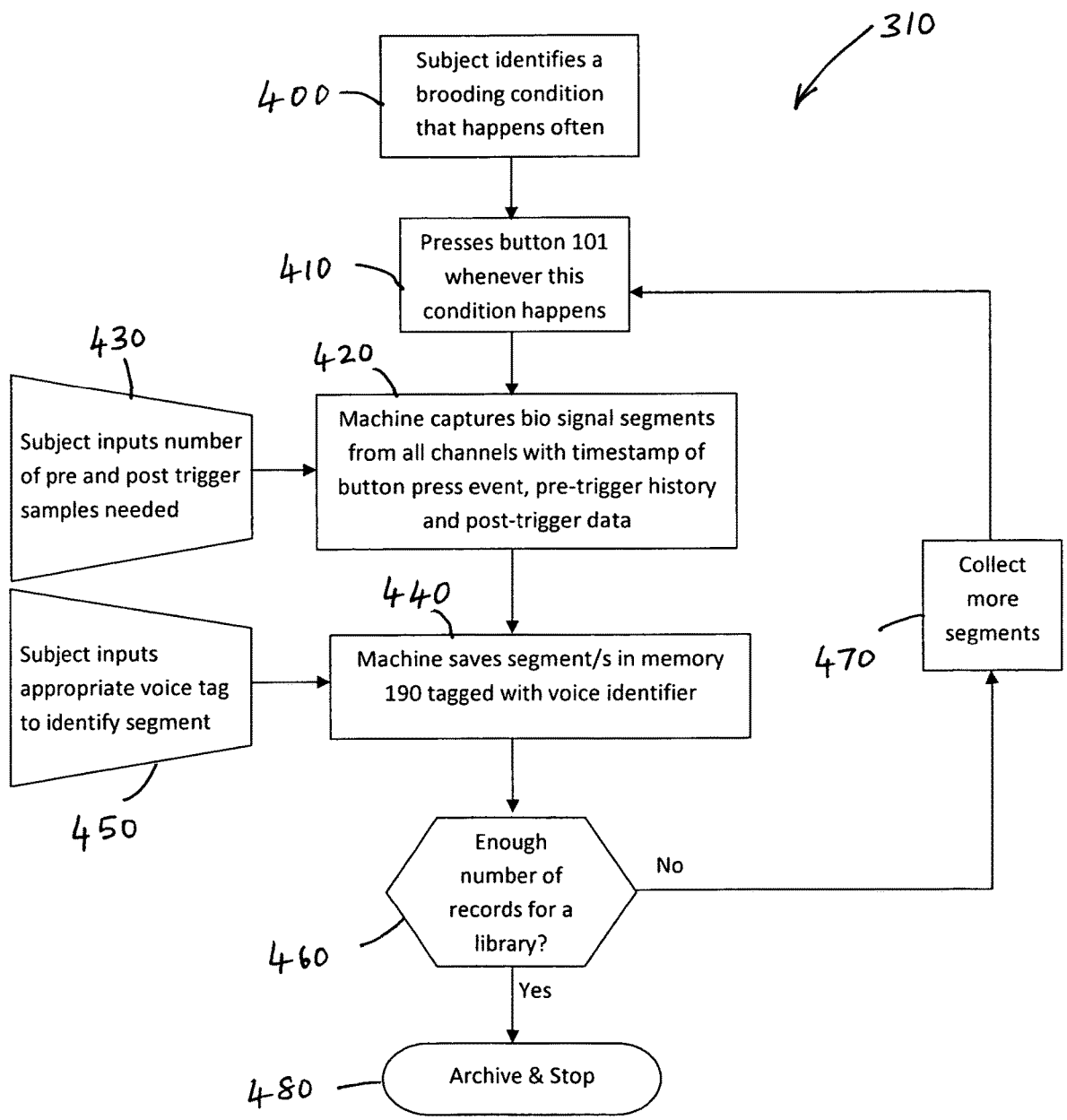
Fig.4- Detail of Block 310 _ Process of Building a Bio Signal Library

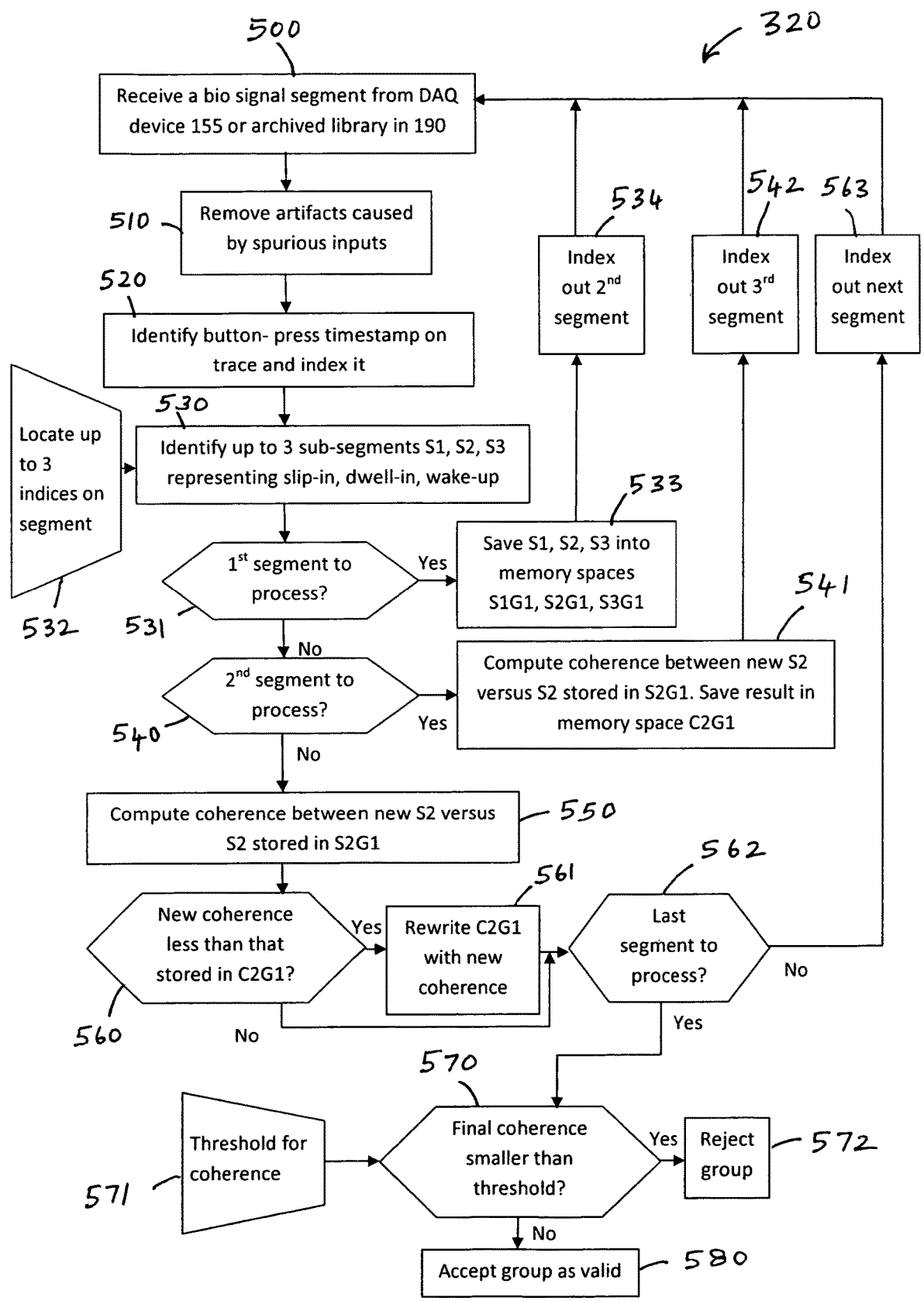
Fig.5- Detail of Block 320 _ Process of Validating a Library

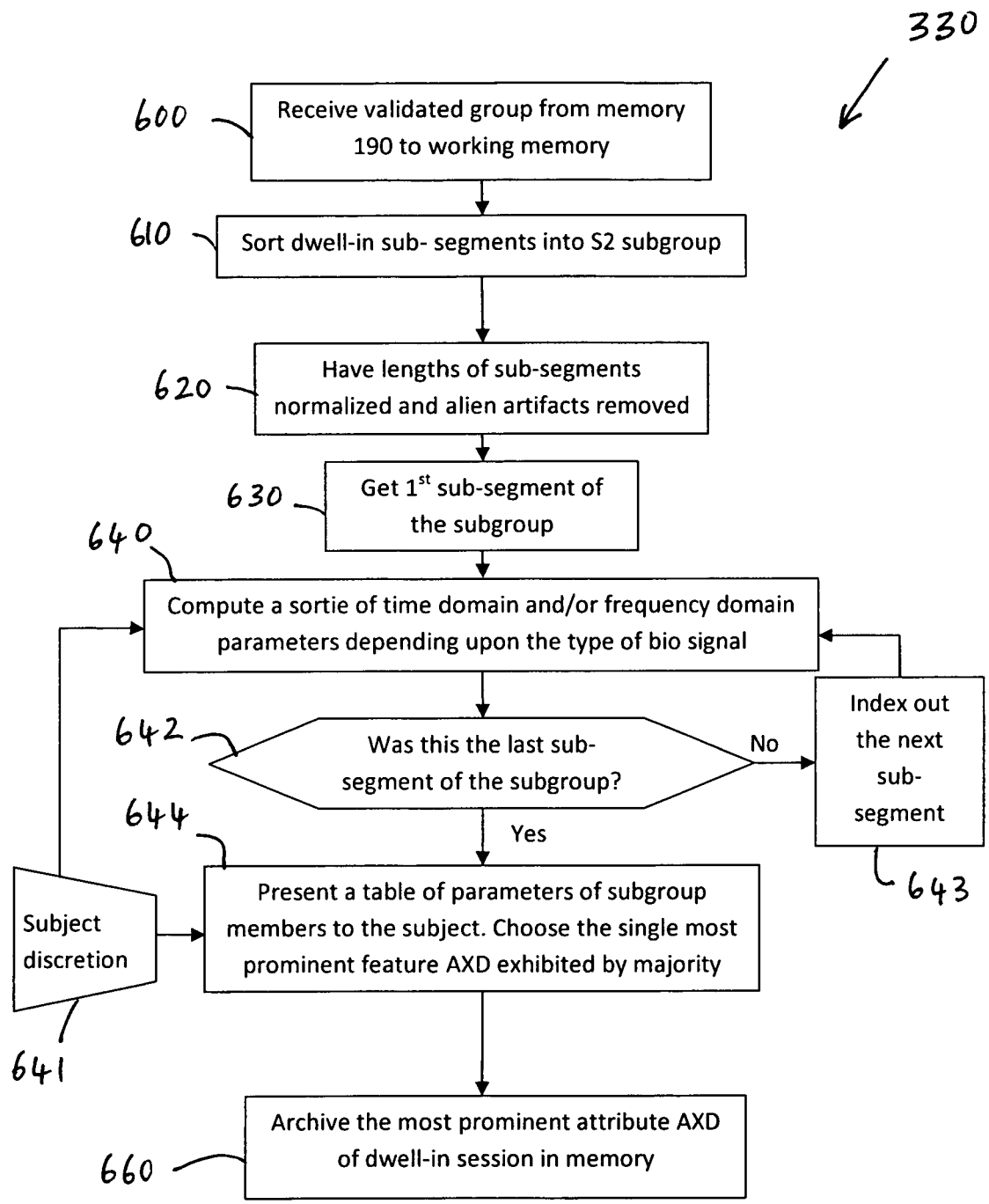
Fig.6- Detail of Block 330 _ Procedure to Characterize Sub-segments

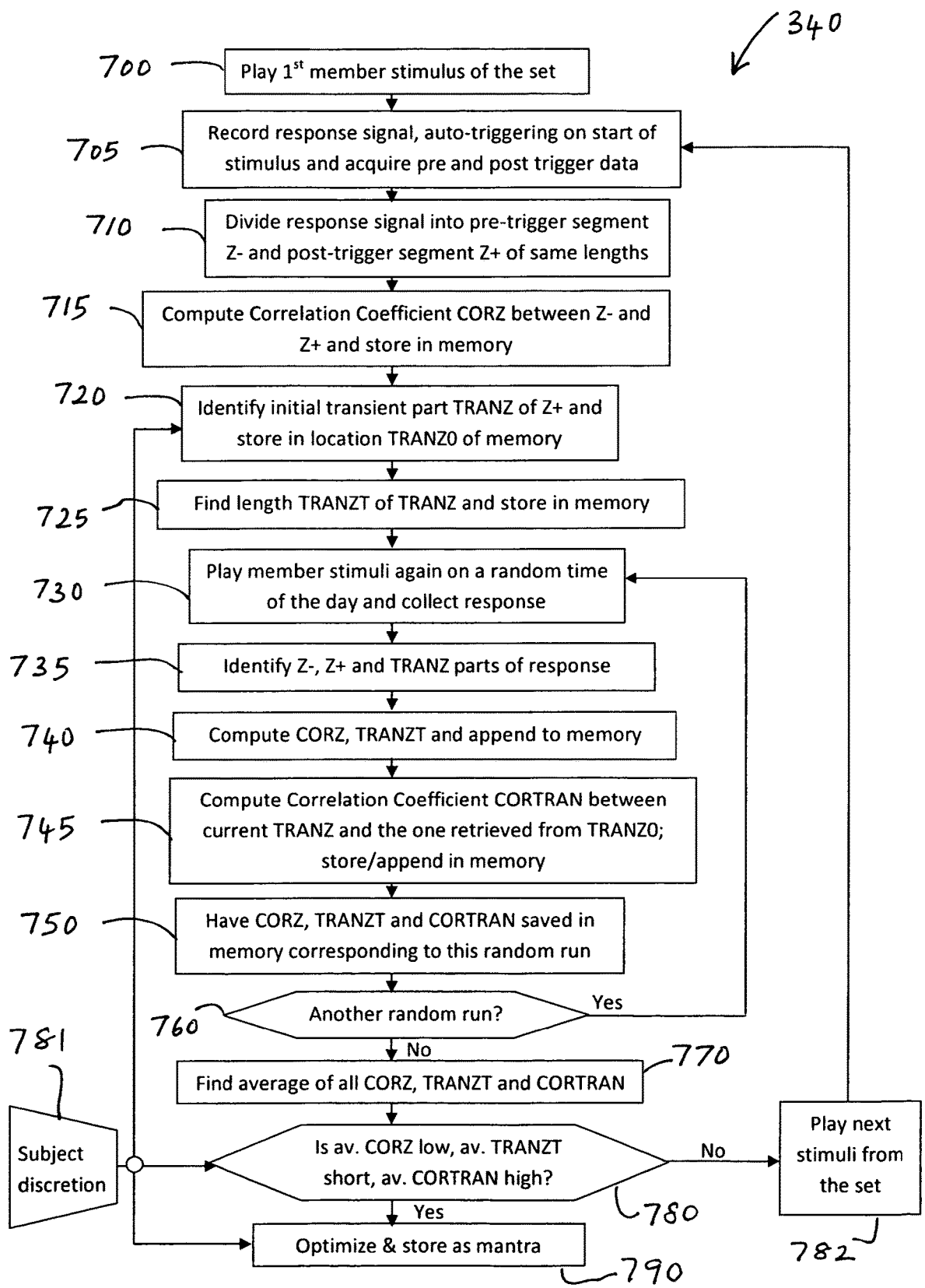
Fig.7- Detail of Block 340 _ Procedure to Select a Mantra

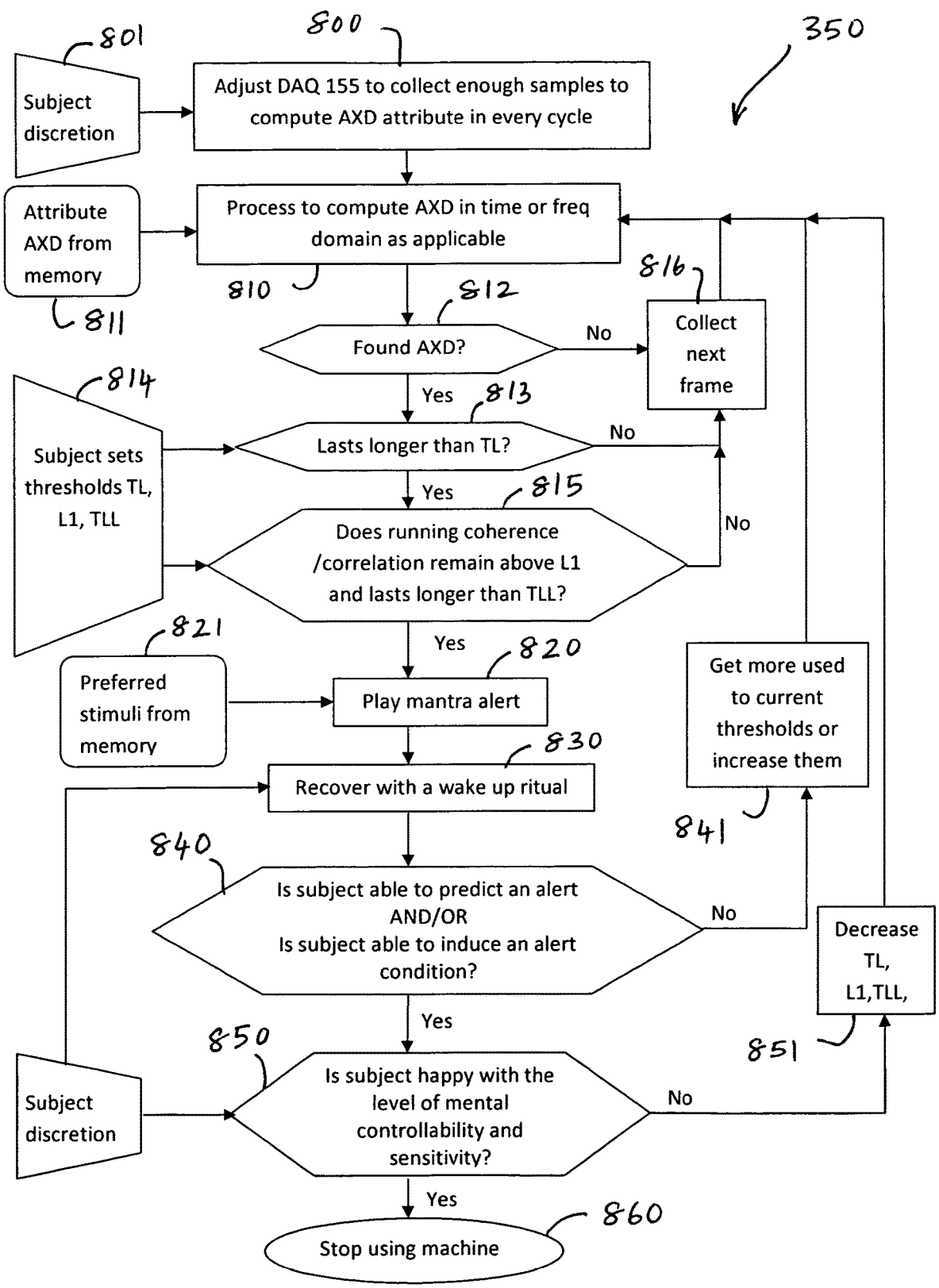
Fig.8- Detail of Block 350 _ Procedure to do Closed Loop Operation

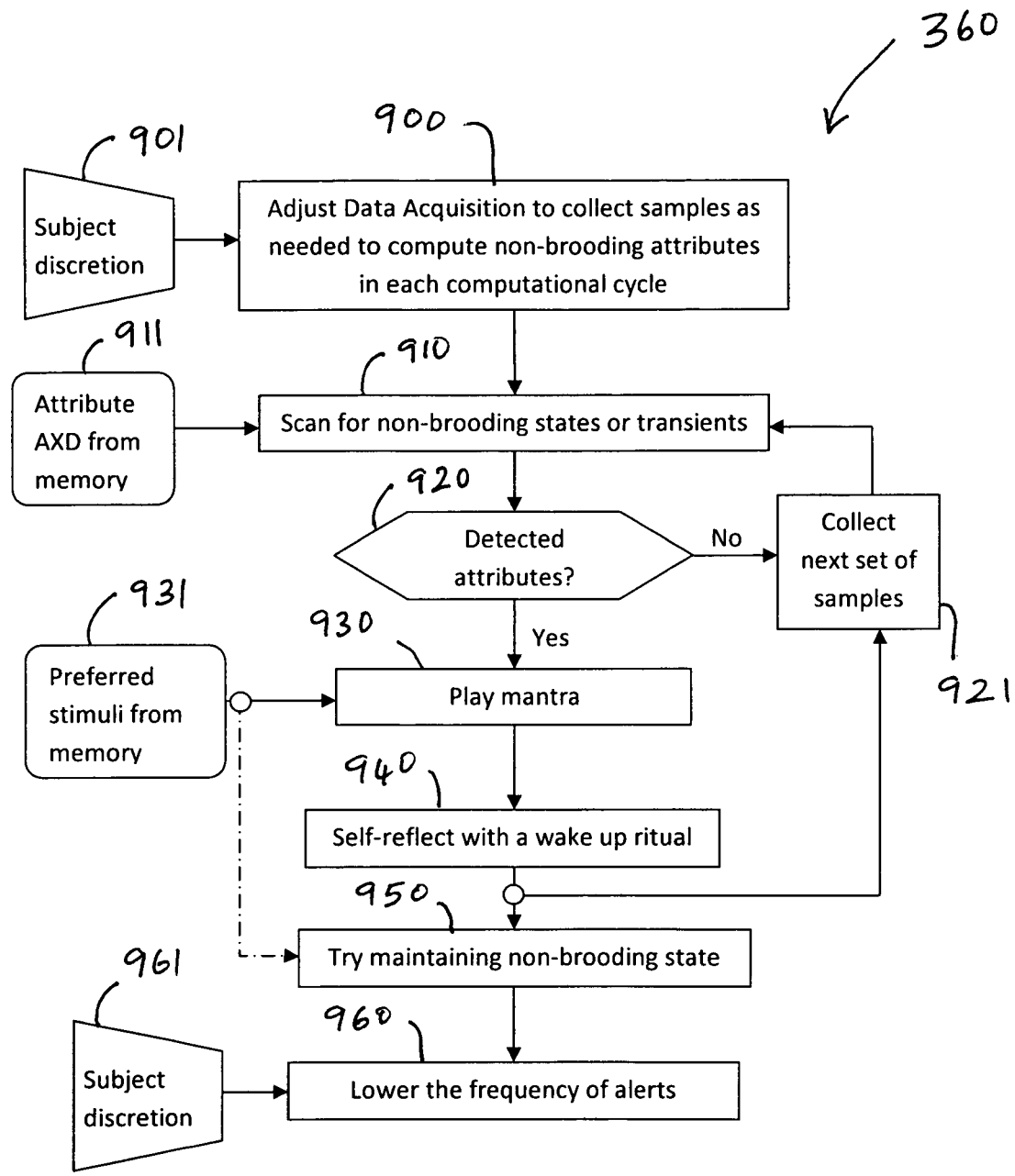
Fig.9- Detail of Block 360 _ Procedure to do Open Loop Operation

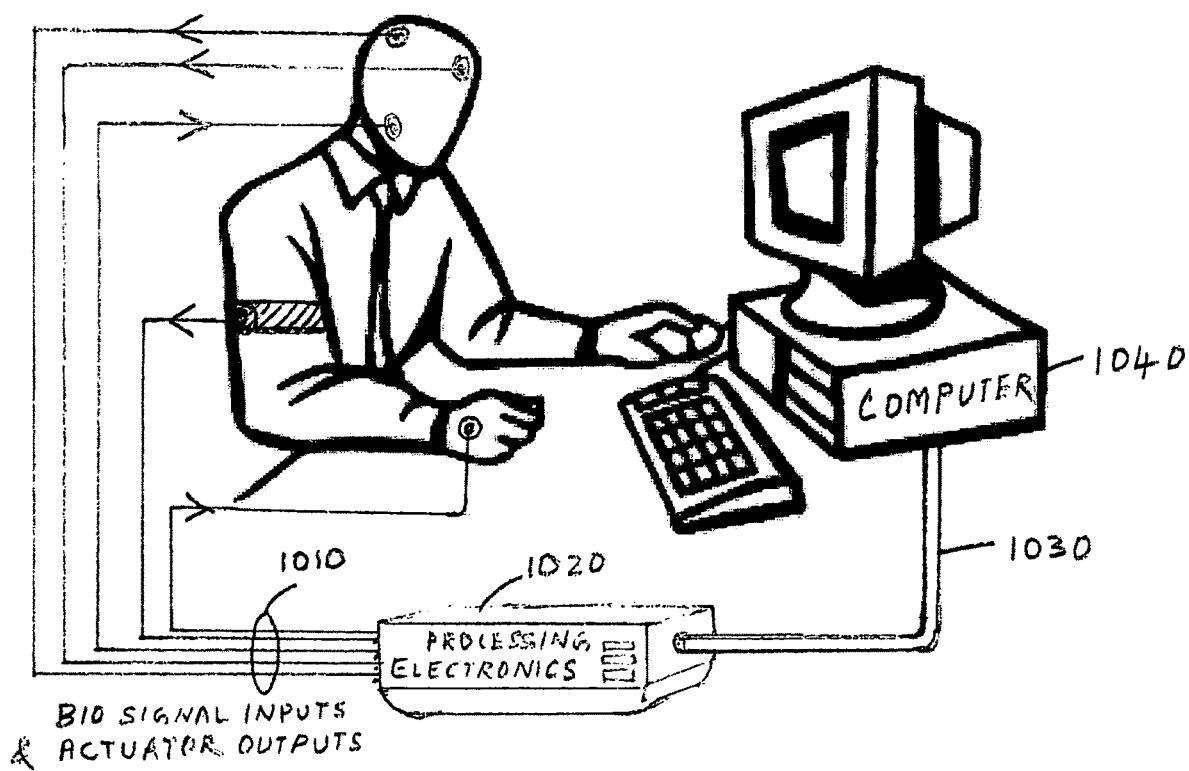
Fig.10- Alternate Embodiment of Mind Strength Trainer

MIND STRENGTH TRAINER

CROSS REFERENCE TO RELATED APPLICATIONS

This application claims the benefit of PPA Ser. No. 61/400,554 filed Jul. 29, 2010 by the present inventor, which is incorporated by reference.

BACKGROUND-PRIOR ART

The following is a tabulation of some prior art that presently appears relevant:

| Pat. No. | Kind Code | U.S. Patents Issue Date | Patentee |
| --- | --- | --- | --- |
| 5,813,993 | A | Sep. 29, 1998 | Kaplan |
| 6,625,485 | B2 | Sep. 23, 2003 | Levendowski |
| 5,724,987 | A | Mar. 10, 1998 | Gevins |
| 5,911,581 | A | Jun. 15, 1999 | Reynolds |

Recently we have been hearing a lot about people coping with mental disorders and syndromes such as ADD, ADHD, PTSD, depression, anxiety, rage etc. In the society we also see increasing signs of stress stemming from intolerance, lack of compassion and emotional instability.

There has been widespread use of antidepressants and antipsychotic drugs to treat several of the above conditions. However, reports suggest that their long term, side and withdrawal effects could indeed make one's life more miserable.

Speaking about the drug-free treatments available, neuro feedback (bio feedback) therapy and psychological counseling are good examples. While they take the right approach in addressing the root cause behind these syndromes (which is, in most cases, a need to strengthen the subject's mind against distractive forces), their effects vain away when the guiding forces from the counselor, feedback machine etc are removed in the long run.

Some setbacks of neuro feedback therapy in the context of ADD/ADHD treatment are listed below:

(f) Neuro feedback therapy relies heavily on rewarding the subjects for their performance during therapy sessions. Unfortunately, those rewarding situations do not happen in real life. So the subjects would not feel motivated the same way in real life.

(g) Rewards are given only for sustaining specific electrical states of the subject's brain. It doesn't reward to differentiate between states (such as between a rewarding state and a non-rewarding state), which is necessary to avoid adverse states.

(h) Therapy is completely 'symptom-based' in the sense that, it only strives to sustain certain levels of β or θ electrical components of brain activity, without paying attention to the subjective mental states underlying those signals.

(i) Not everyone stays motivated to play the same type of neuro feedback game till the end of session that typically involves several sittings and fine tuning.

(j) It is expensive, long winding and its success depends on how good the trainer is.

Meditation techniques have long been a proven remedy for the mental disorders mentioned above. Meditation is also known to successfully treat conditions of mental degradation with symptoms such as, lack of concentration, lack of memory etc. Of all the meditation techniques available out there, the ancient mantra meditation technique is known to give effortless and superior results. Transcendental Meditation™, Primordial Sound Meditation™, NSR Meditation™ etc are variations of mantra meditation.

Mantra meditation can be viewed as a highly sophisticated and personalized neuro feedback session where the feedback is played out in the mental domain as opposed to the electrical domain of electroencephalogram (EEG) signals. In mantra meditation, rising of a mantra in subject's mind in response to a deviation in mental state, could be thought of as a self-reward. In other words, mantra meditation is a mental game wherein, mind acquires the skills to supervise, alert and reward itself. As the subject progresses through several meditation sessions, the reward merges with the goal (which is a certain mental state) itself. Further down, the goal ceases to exist as the subject's consciousness tends to merge with the goal. As it is obvious to any person skilled in practicing mantra meditation, it has the advantage that rewards (mantras in this case) do not depend upon any external world stimuli. Besides, mantras being extremely personal experiences for the subject, and having the ability to self evolve, stay 'magical' and 'eternal' in subject's mind.

All being said about meditation (and mantra meditation), it is not so easy to impart this skill to someone. While there're numerous ways to demonstrate, lecture and facilitate meditative conditions (such as through instructional classes, video and audio media, yogic practices, chanting sessions, breathing practices), they don't help much unless the subject is extremely motivated in reflecting on his/her own states of mind. The most phenomenal success in teaching mantra meditation was achieved by late Maharishi Mahesh Yogi through his acclaimed Transcendental Meditation™ technique.

However, teaching of Transcendental Meditation™ has been having three major difficulties:

(d) Choosing of mantras with limited or little knowledge of the subject's personality and history.

(e) Lack of means to monitor or challenge the subject's mind when it is inside a meditation session.

(f) Not being able to motivate ordinary people to make them aware of their mental abilities to get them started on at least a starter session.

Careful examination of the art has revealed to the inventor that gaining ability to controllably flex mind between known, distinct mental states gives a tremendous jumpstart to the subject on the path to learn mantra meditation. Making ordinary people aware of their 'mental muscles' and exercising those muscles on a daily basis is perhaps the best way to spread its popularity.

There have been efforts to develop machines that monitor mental states and alert users upon state transitions for various purposes (U.S. Pat. Nos. 5,813,993, 6,625,485, 5,724,987, 5,911,581). Work reported in the field of sleep-alert continuum characterizations is a good example of such efforts. These techniques are generally seen to have the following setbacks:

(g) They rely heavily on creating (and identifying memberships functions of) input classes of bio signals which are collected under idealized conditions far moved from reality.

(h) They rely only on EEG signals and their frequency components.

(i) Physical conditions are given more importance than the underlying moods (mental states) of people under test.

(j) Temporal variations and individual to individual variations in bio signal activity aren't adequately modeled.

(k) Alerts are open-ended in the sense that, they couldn't be programmed by the user to reveal a causal relationship between the underlying thoughts (mental states) and the alert itself.

(l) Alerts used have been impersonal in the sense that there hasn't been any effort to control the quality of those alerts based on individual feelings.

As discussed above, there haven't been procedures or technologies out there to monitor, alert or controllably flex human minds in order to attain supervisory abilities all along the subjects' wakened life even without the help of external instruments.

SUMMARY & OBJECTIVES

The present invention is a collection of algorithms and control system components, some of which can be combinatorially used in training a human mind to develop instincts to flex mental state in response to onset of electrically identifiable mental events. It has hardware and software means to excite a subject's senses with a variety of types of bio stimuli, collect a variety of types of bio response signals in response to mental states or said stimuli, tag the collected signal segments, identify patterns underlying specific mental states and process bio signals in real-time to calculate required bio stimuli outputs in user-interactive or automated environment.

An objective of the invention is to prepare human mind for easy and more effective learning of mantra meditation technique, which involves the following steps

(12) Manually triggered recording of bio signals from subject's body in tandem with recognition of at least one of two disparate states of subject's mind (called brooding and non-brooding states) per judgment by the subject himself/herself.

(13) Building up libraries of similar bio signals collected under similar mental states personally experienced by the subject and aided by algorithms

(14) Using algorithms to process and characterize parts of collected bio signals so that common traits of dwell-in, slip-in and wake up sections can be identified for each library.

(15) Using machine and algorithms to continuously monitor subject's mind for signs of steady states (dwell-ins) or transients (slip-ins and wake ups) helped by traits characterized before.

(16) Determining appropriate mantras for the subject by scientifically evaluating various bio stimuli based on their ability to 'surprise' the subject.

(17) Alerting subject using appropriate mantras upon signs of dwell-ins and/or transients outlasting a set threshold

(18) Pavlovian conditioning of subject's mind on causal relationship between mantra and sustenance of the preceding mental state.

(19) Instructing the subject to follow a personally configurable 'wake-up ritual' upon hearing (or feeling) mantra

(20) Challenging subject with mental games where subject would beat the machine to playing alerts or artificially create brooding or non-brooding states at progressive threshold settings

(21) Preparing the subject with a controllably deflectable mind and a set of favorite mantras and devoid of any external equipment

(22) Continuing training until virtual (perception of) mantras take over the place of real world stimuli Another objective of the present invention is providing a better method to identify, sort, analyze and correlate bio signals collected from a human's body at various occasions. This is based on a trigger-mark manually set by the subject upon recording.

Another objective of the present invention is providing a superior method of forming classes of bio signals aided by recurring personal moods of the subject rather than mere electrical characteristics of signals.

Another objective of the present invention is providing a method to analyze and threshold signals based on their trending, that is, duration of patterns rather than amplitudes in the temporal or spectral domain.

Yet another objective of the present invention is usage of bio signal libraries not limited to EEG for analyzing mental states.

And yet another objective of the present invention is providing an algorithm to evaluate and synthesize bio stimuli (known as mantras in the context of this patent) with emphasis on personalizing its effects based on analysis of subject's feedback as well as bio signal responses.

A final objective of the present invention is providing an algorithm to condition human mind on a causal relationship between certain bio stimuli and non-brooding mental states so that playing of such stimuli triggers positive thoughts.

DRAWINGS—FIGURES

FIG. 1 shows a portable Mind Strength Trainer in accordance with the $1^{st}$ embodiment.

FIG. 2 shows electrical schematics of a Mind Strength Trainer.

FIG. 3 is a top level operational flowchart of the device made of block diagrams.

FIG. 4 is a flowchart that has block diagrams describing the process of building a bio signal library.

FIG. 5 has block diagrams describing the process of validating a bio signal library.

FIG. 6 describes the process of characterizing signal sub-segments in order to find their common attributes.

FIG. 7 is a flowchart describing the process of selecting a suitable mantra.

FIG. 8 has block diagrams depicting how the device operates in closed-loop mode.

FIG. 9 has block diagrams showing the open-loop mode of operation of the device.

FIG. 10 shows a second embodiment of the invention, which is not portable.

DETAILED DESCRIPTION—FIGS. 1 AND 2—FIRST EMBODIMENT

FIG. 1 illustrates the $1^{st}$ embodiment of a Mind Strength Trainer which is in the form of a portable headset device 100. Central to this embodiment is a human subject 10 wearing the headset device. The device primarily comprises of at least one bio actuator 120, at least one bio sensor 150 and signal processing electronics (such as signal conditioning & data acquisition electronics 155, actuator-driver 125 and signal processor 170) that channel signals between sensors and actuators. In FIG. 1, the bio sensor 150 used is a dry EEG (electro encephalogram) sensor electrode that collects EEG signals from subject's body and channels it through signal processing electronics. The bio-actuator 120 is a headphone that plays mantras 110 in the form of audio-stimuli into subject's ears. In a most general sense, mantra 110 is a methodically engineered bio stimulus, defined in the context of the present invention. It is depicted as a non-physical entity in FIG. 1. Another important element of the present invention are two disparate states of subject's mind called the brooding 160 and non-brooding 170 mental states which causes change in the EEG patterns that control this device. Concepts of these non-physical entities (brooding states, non-brooding states and mantras) are explained below in order to better understand the working this embodiment.

Human mind has a tendency to get lost in emotional cycles. There are occasions when we forget the time and indulge in self-feeding thoughts as negativity consumes our minds. Most often, rumination cycles set in when we are left to ourselves such as in rest rooms, office cubicles or cars. Several minutes or even hours easily lapse if we succumb to cyclic thoughts. While we know that they don't produce any useful outcome and are even detrimental to our emotional wellness, it is hard to control or predict their onset. For example, there are times we can't remember how and why the last 'fit of rage session' happened or how often we slip into 'self indulging thought sessions' or how negative emotions build up upon seeing a person. In the context of this invention, these states are termed brooding states of mind while the associated life events are called brooding sessions or brooding events. The signature of a brooding session is cyclic ruminations where the subject goes over thoughts and feelings the same way over and over again, for no reason and having no control.

We also have exuberating moments in life, on the other hand. They're filled with unconditional joy and have traits almost opposite to that of brooding sessions. They are relatively short, contain no self-reflecting components and are never cyclic. They are more like a child-like exhilaration where we're happy for no reasons and about everything around us. These events are called non-brooding sessions and the associated mental states are called non-brooding states, in the context of this invention.

Human beings connect to their surroundings through their five senses. And we know there are some sensory stimuli, so powerful that they can completely deflect or de-rail our thoughts and moods irrespective of our mental states. For example, a lovely music note or smell of pine trees or a cold shower can pull you out of a depressing thought. Similarly, a deafening alarm, cry or a disgusting smell or sight can completely throw you off track. Mantras in the context of this invention are bio stimuli applied to various human senses with the intent of breaking brooding cycles or alerting changes in mental states. These are methodically engineered signals that can impart an always likeable, surprise element to the user of the current invention.

Going back to the embodiment of FIG. 1, it may be noted that sensors and actuators of various types suiting individual's sensory input and output—preferences may be used to achieve the intended results. However it is imperative that signals sourced from said sensors exhibit a certain measure of correlation (higher than a threshold level) with the mental states of the individual wearing the device. A 'higher than threshold level' correlation is said to exist between a certain type of signal and the underlying mental state of the individual wearing the device, if segments of said signal collected from said individual during said mental state at disparate occasions exhibit a magnitude of mathematical correlation larger than a previously set threshold level when computed between themselves as opposed to signal segments collected from other mental sessions (states). The exemplified bio sensor in FIG. 1 is of dry electrode EEG type, such as the ones developed by NEUROSKY of USA or IMEC INTERNATIONAL of Belgium or EMOTIV SYSTEMS of Australia with signals tapped from one location or simultaneously from multiple locations of subject's head. A preferred bio actuator suitable for the embodiment is a pair of headphones optionally having noise canceling features. In the preferred configuration, the headphone also plays menu items to the subject when the device wants to interact with the subject.

In the preferred configuration, device 100 has a button 101 to record brooding events, a second button 102 to record non-brooding events and a third button 103 to choose the operating mode of the device. It also preferably has a micro-phone 104 to take voice inputs and at least one communication port 105 such as USB or Bluetooth® to interact with a display device or external computing devices or a network. Also it is important that the button-press events be able to trigger the channels handling signal-acquisition, so that the acquired signals can be time-stamped in synch with said button-press events and stored in memory as data segments containing adequate amounts of pre-trigger, in-trigger and post-trigger history.

FIG. 2 provides an electrical schematic of the 1st embodiment. Though this depiction portrays only one EEG channel for bio signal input and one audio channel for bio actuator output, it may be remembered that in practice, a multitude of sensor and actuator types could be chosen, combined, deployed, and tuned as preferred by the user 10. For example, a plurality of sensors of similar type (such as multiple EEG sensors tapping from multiple locations of the subject's head as described in the first embodiment) or dissimilar types (such as an EEG sensor and a skin conductance sensor working simultaneously on subject's body) could be combined and tuned as suiting to an individual. Typical bio sensors available are EEG, EMG, skin conductance, breath rhythm, voice, and cochlear response sensors, kome kami switches etc. If acceptable to the subject, bio sensors could also be embedded into the subject's body to directly tap neuro signals.

Bio actuator 120 together with driver 125 are designed to drive stimuli such as audio, video, smell, taste and tactile stimuli, capable of capturing the attention of the human subject. As in the case of bio sensors, bio actuators of similar or dissimilar types could also be simultaneously deployed on subject's body to the preference of the individual. If acceptable to the subject, bio actuators could be embedded into the subject's body to directly stimulate the neural system. Together with control logic inside processor 170 (which determines when or whether to drive the bio actuators), they form an alerting mechanism for stimulating the subject.

In FIG. 2, the data acquisition device 155 electrically communicates with bio sensors 150 and is capable of acquiring data from the using configurable triggering modes in time domain. Together, they form a signal channeling means that stream data to the device in real time.

The device also comprise of a memory 190 able to receive, store and retrieve data pertaining to signals and stimuli in various pre-designated groups and communicating with said data acquisition devices and said bio actuators via processor 170.

An important part of the embodiment is a set of 'preferred' stimuli patterns driving actuators 120 in order to pleasantly jolt human consciousness. Members of this stimuli group are systematically tested on the user to statistically identify the most effective and consistent (or the 'optimal') ones, that suits the user's personality. Such optimal stimuli identified, are also called mantras 110 and are stored in the operating memory 190 of the device. In the operating phase, the device's selector mechanism can randomly change the mantras that fire, to enhance the personal experiences of the user.

An extremely important part of this invention is a conditioning mechanism (habituation logic) built into the closed-loop operational algorithm of the device illustrated in FIG. 8. This logic provides a game-like environment, where the user's mind gets habituated to experiences of controlled length. As the user gets used to the device's ways, the habituation logic challenges him/her to anticipate an alert stimulus. In other words, it trains the subject's mind to self-awaken from brooding states by virtue of self-generated alerts. Eventually, this leads to the ability to automatically reflex away from non-productive states even without wearing the device.

Also stored in memory 190 is a number of operational states 122, able to associate each said machine task to at least one operational state of the machine. Memory 190 also hosts various signal processing algorithms and an operating system that runs the device.

An interactive interface 180 optionally consisting of display, touch screen-input and menu items able to communicate user settings and preferences back and forth between user and the machine via one of communication ports 105 is provided. Additionally, there are buttons 101,102 and 103 provided on the device to enact quick action short-cut functions (such as On/Off, Record, Stop, Toggle menu items, Change operating modes etc).

The user is also able to interact with the device by means of voice communication, by hearing operational instructions through headphone 120 and responding through microphone 104.

A memory controller 191 communicating directly with memory 190, and indirectly with user interface 180, data acquisition device 155 & bio stimuli drivers 125 is also provided.

Central to this schematic is signal processor 170 communicating with data acquisition device 155, bio actuators driver 125, memory controller 191, user interface 180 and the buttons 101,102 & 103.

Operation—FIGS. 3,4,5,6,7,8 and 9—First Embodiment

Overall Operation of the Device:

FIG. 3 is the top level flow chart for the operation of 1$^{st}$ embodiment of the invention when it is used to train human mind to controllably flex between mental states.

Wearer (subject or user) of a Mind Strength Trainer (the device or machine) starts off by setting it to Learning Mode 300 by pressing button 103. From there subject has a choice to branch out to path 301 (where he/she learns to sense their brooding moods) or path 302 (where subject tunes to his/her non-brooding moods) or do both. In any case, subject needs to complete path 303 (selecting mantras) before switching to Operating Mode 342.

The first step in pursuing paths 301 and 302 is building a library of bio signal segments (EEG signals in the context of the 1$^{st}$ embodiment) by the subject, which is represented by blocks 310 or 311 in FIG. 3. The procedures represented by blocks 310 and 311 are identical in nature and are further elaborated in FIG. 4 flowchart. The libraries thus built are validated (blocks 320 and 322 of FIG. 3) by the machine and the validation process is explained in FIG. 5. Members of a validated library will have similar trends, shapes, durations and attributes. Members may comprise of up to 3 sub-segments corresponding to slip-in, dwell-in and wake up sessions of the subject's mind. After a library is validated, the machine separates and characterizes (block 330 or 324 in FIG. 3) sub-segments using their time domain or frequency domain traits. Process of characterization of sub-sections is elaborated in FIG. 6.

As a sub-process within the Learning Mode, subject can switch to a Mantra Finding Mode by initiating path 303 of FIG. 3. Mantra Finding comprises of an initial manual screening (blocks 332 and 334) of variety bio-stimuli by the subject, which has the following steps:

d) Loading memory 190 with libraries of bio stimuli signals that are appropriate for the chosen bio actuators 120 and drivers 125. Smell of pines or a bird's tweet or feel of breeze are examples. For the current embodiment audio clips comprising binaural beats or musical sounds may be chosen.

e) Receiving feedback from the subject regarding their pleasantness and memories they trigger each time the stimuli is played.

f) Picking out (a set of) favorite stimuli of all such times as identified by the subject having maximum pleasantness and minimal afterthoughts.

After this initial screening, the machine evaluates (block 340 of FIG. 3) the selected stimuli using an elaborate algorithm flowcharted in FIG. 7. Outcome of this procedure (the most favorite candidates for mantras) are further engineered to enhance their surprise appeal and archived back in memory 190.

Once the device is trained to identify the slip-in and dwell-in sessions of targeted mental states and it has the most suitable mantras in store (block 341), it is ready to end the Learning Mode and start the Operating Mode (block 342) of the device.

Per block 343 of FIG. 3, subject needs to choose if he/she wants to pursue an open-loop operation 360 or closed-loop operation 350 of the device. To make this choice, it is important for the subject to judge which moods he/she encountered were of identical (if not of similar) nature, repeating in natural life and if the collected signals were of high integrity in terms of coherence & confidence interval. The machine aids the judgment process by displaying the library members, associated voice tags and computed confidence intervals. The voice tag attached to a segment helps the subject remember the circumstances under which he/she collected that particular bio signal. If subject feels that he/she nailed the brooding states better than the non-brooding ones, he/she would pursue the closed-loop path which is a more desirable way of operating this device. On the other hand, the subject would opt for the open loop operation.

Block 350 of FIG. 3 represents the closed loop mode of operation which is further explained in the flowchart of FIG. 8. The open loop operation (block 360) is flowcharted in FIG. 9.

The subject chooses when or if he/she would stop using the device. In the case of closed loop operation, the subject progresses through levels of mental games where the subject's mind is made progressively sensitive to subtler changes in mental states. Eventually, the subject is able to carry mantras in his/her minds and gain supervisory abilities at all times, without a need for an external device (block 351) to monitor or alert. In the advanced levels of these games, mantras play instinctively inside subject's mind to ward off brooding states, even with the device's output stimuli turned off.

As in the case of closed loop operation, subjects undergoing open loop training are also able to establish causal relationships between their moods (non-brooding, positive moods in this case) and stimuli generated by the device. In both the cases, they gain ability to reflect on their mental states and learn to remain in non-brooding states than in brooding conditions.

In the following sections all the major algorithms & procedures used in the main flow diagram of FIG. 3 are explained.

Procedure to Collect Bio Signals:

FIG. 4 explains how a bio signal segment is collected from subject's body, entirely at the discretion of the subject. This flowchart and the following description pertain to brooding states of the subject. It may be borne in mind that the same procedure is used to capture non-brooding states too.

As the first step (block 400), the subject would identify situations in life when he/she gets lost in thoughts occasionally (if not frequently). Examples are some regular chore sessions (morning commute, restroom time, in front of shaving mirror, brushing teeth etc) when you're left to yourself. Else, it could be certain occasions that trigger your brooding thoughts such as, after meeting with your boss, thinking about a lost love, a missed opportunity, self-hate or self-admiration sessions etc. Another example is subjects being thrown into a bad mood upon encountering a certain race. Subject starts wearing the device in its Learning Mode and when he/she realizes that he/she is caught in a brooding session, he presses (block 410) an easily reachable Record button 101 on the headset. Alternately, in case he/she find himself/herself in a distinct non-brooding situation, he/she presses button 102 which is preferably located disjoint to 101. In a preferred configuration, buttons 101 and 102 could be on the left and right sides of the headset.

As the subject presses the Record button, the device captures a segment of bio signal (EEG in this case) that encompasses the trigger event (manual button pressing event), pre-trigger history (past signal representing brooding) and post-trigger data (signal representing woke-up state of subject's mind). Length of pre-trigger history is pre-set to a high value (several minutes) so that a possible sign of slipping into the brooding state could be captured and contrasted against the dwell-in period. It may be noted that the final portion of pre-trigger history would comprise of EEG activities that reflect a waking up of subject's mind (which happens when subject realizes that he/she had been ruminating for a while) followed by the button pressing event itself. Post-trigger data captured is programmed to be a shorter one, which would comprise of subject's woke-up mental states. Per 430, subject also has the ability to choose the signal segment size and size of the buffer needed to store data in each capture.

After pressing the record button, the device prompts the subject 10 to add (block 450) a voice tag to the segment that would be archived along with the segment which would later be of assistance to identify the event type. For example, subject could say "had been thinking about so and so during the morning commute" etc. This input will be accepted via microphone 104 of FIG. 1 embodiment. Subject can build simultaneous libraries grouped according to their contexts or stick to a singular type of event.

Subject 10 is preferred to wear the device for several days or weeks until he/she feels confident that he/she has encountered and captured enough number of brooding situations of similar (if not identical) nature.

Procedure to Validate Libraries:

Following steps explain how a signal library (and hence, members within that library) is validated by the machine. The validation procedure comprise primarily of mathematically checking for similarity between segments of signals within the library, with assistance from the subject in choosing situations having most similar underlying moods. If the machine finds difficulty in quantizing similarities, the subject or a field expert would guide the machine through the process by suggesting threshold levels etc. Validation of library and training of machine on a validated set improves the quality of mental state detection during machine operation.

FIG. 5 shows the operational flowchart of validation procedure. It comprises of:

s) Loading (block 500) the first EEG segment of the library into working memory space from an archival (in post-processing mode) or directly from the data acquisition device (for real time operation, if the subject feels like processing signals right away)

t) Removal (block 510) of spurious artifacts caused by eye-blinks, EMG activity etc from the segment u) Identification (block 520) of 'button press' event on the time series and indexing it as N1 v) Receiving (block 532) inputs M, O and P (three indices) from the subject to split (block 530) the signal segment into up to 3 sub-segments representing 3 regions of mental activity within the captured brooding session. Determining M, O and P is an interactive operation where the subject 10 is presented with a visual display of the signal trace via interface 108 of the device. If sufficient pre-trigger history has been captured, the subject will be able to identify a slip-in transient (to be called S1 sub-segment) in the earlier section of the trace where he/she drifted into the brooding mood. If not, subject might see only the steady state sub-segment S2 (corresponding to the dwell-in session of the brooding state) and the transient sub-segment S3 (corresponding to waking up from the brooding mood). M, O and P are essentially indices of the boundary points that define the three sub-segments.

w) Marking an $M^{th}$ sample before the trigger point (N1$^{st}$ sample) in said time series so as to define a contiguous sub-segment S3 consisting of signal samples N1-M through N1-1 representing a wake up session of mental activity x) Marking an $O^{th}$ sample before said N1$^{st}$ sample in said time series so as to define a sub-segment S2 consisting of samples N1-O through N1-M−1 representing a dwell-in session of mental activity y) Optional marking of a $P^{th}$ sample before said N1$^{st}$ sample in said time series so as to define a sub-segment S1 consisting of samples N1-P through N1-O-1 representing a slip-in session of mental activity z) Saving (block 533) sub-segments S1, S2 and S3 into pre-assigned memory spaces S1G1, S2G1 and S3G1 in memory 190 aa) Loading the $2^{nd}$ signal segment member from the library, splitting it into up to 3 sub-segments (say S1', S2' and S3') in the same way as done with the 1$^{st}$ segment bb) Computing a coherence array C2 between S2 and S2' and storing in memory space C2G1 where S2 is a sub-segment of the previous member of the library, recalled from memory space S2G1. Coherence is computed after dividing each of sub-segments S2 and S2' into windows having sufficient lengths to contain multiple cycles of EEG patterns. As it will be evident to anybody familiar with digital signal processing, windows within S2 & S2' need to be of same length, suitable windowing function need to be applied and FFT parameters need to be chosen to compute coherence. Subject has the freedom to choose such parameters (such as type & size of window, overlap, number of FFT points) or can leave them at expertly chosen default levels. Computed C2 will be an array of numbers between 0 and 1.0 representing the coherence function (one-sided, magnitude squared coherence) between the sub-segments at various frequency steps of interest. While at least two windows per sub-segment are necessary, a higher number of windows improve the confidence interval of coherence computation.

cc) Continuing this process on the $3^{rd}$ member signal of the library by identifying at least a dwell in session sub-segment, dividing it up into windows and computing its coherence C2 against S2 recalled from memory space S2G1 dd) Comparing (block 560) the newly computed coherence array C2 of step 'k' with saved array in memory space C2G1 of step 'j'. To compare the two arrays, a statistically derived representative value per array (such as median or average) may be used. Also, it is desirable that confidence intervals behind the computation of the two arrays are comparable.

ee) Keeping contents of memory space C2G1 intact, if newly computed values of C2 is equal or greater than the stored ones in C2G1 ff) Replacing contents of memory space C2G1 with the new array of C2 if it is lower than the stored array in C2G1 gg) Continuing processing of every member signal in the library by computing coherence C2 of dwell-in sub-segment against the stored sub-segment S2 retrieved from memory space S2G1, and writing memory space C2G1 with lower of the computed value of coherence array.

hh) After processing the last library member, comparing (block 570) of final contents of memory space C2G1 (i.e., comparing the statistically representative value for the array) against a subject inputted threshold level T for expected coherence number.

ii) Rejecting (block 572) the library, discarding all signals within and starting over with a new population of bio signals, if finally stored coherence numbers are lower than level T jj) Accepting (block 580) the library as valid and archiving it to memory 190 if final C2 is equal to or higher than user defined threshold T with a reasonable confidence interval.

Procedure to Characterize Bio Signal Segments within a Validated Library:

After building a robust library (or libraries) of brooding (and or non-brooding) states, the next step is finding a common pattern inside all members of the library, so that it can be used as a sign to search for similar mental states. For example, all validated S2 sub-segments of the library would bear characteristics reflecting a brooding state of subject's mind. FIG. 6 is a flowchart depicting steps (blocks) involved in the characterization process that determine attributes that are most common to the sub-segments. Common time-domain attributes (transient shapes, rise/fall times, DC levels etc) and frequency-domain attributes (frequency components, power spectral density for a certain frequency bin, area under PSD curve in a frequency band etc) are computed on the sub-segments, tabulated and presented to the subject via user interface 108 (blocks 640, 641,642,643 and 644). Thus the machine helps the subject choose (blocks 644 and 660) the 'best' attribute available (named AXD) to represent the dwell-in session of his/her brooding state.

Procedure to Select an Optimal Stimuli:

As mentioned in the early part of specification, after the subject identifies a set of his/her favorite stimuli, the device 100 goes on to evaluate (block 340 of FIG. 3) them as flowcharted in FIG. 7 to choose the ones that have optimal effects on the individual. An optimal stimuli (also known as a mantra in this context) is a stimuli that (a) can alter the mental process of (or in other words: capture the attention of, or distract, or surprise) a subject in a pleasant way and (b) maintains its distractive power satisfactorily over hundreds of repetitions. FIG. 7 depicts the typical signal-processing steps involved in choosing optimized mantras. From the foregoing discussion it would become clear that acceptance levels for the optimization parameters CORZ, TRANZT and CORTRAN used in the optimization process are highly subjective. A first stimulus (audio clip in the present case) is chosen and played at random times of the day, for several days and corresponding bio responses (EEG signals in the present case) from the subject's body are recorded by the device each time. The intent here is to surprise the subject with stimuli at most unexpected situations, collect the bio responses and check if the quality of bio response degrades with time. The capturing process (block 705) is auto-triggered by the stimuli so that a pre-trigger (pre-stimulus) segment 'Z–' and a post-trigger (post-stimulus) segment 'Z+' of equal length are obtained. With help from the subject, an initial transient part of 'Z+' is identified as TRANZ which encompasses the 'moment of surprise' caused by the unexpected stimulus. Segment TRANZ obtained from the first run is archived (block 720) in location TRANZO of memory 190. Further, two parameters are computed on the 1st bio response and saved in memory 190. They are a Correlation Coefficient CORZ calculated between segments 'Z–' and 'Z+' and TRANZT which is length of segment TRANZ.

From the 2nd run onwards, a new parameter called CORTRAN is computed to check if TRANZ part of the current run has any resemblance with that collected in the original (1s') run. CORTRAN is the Correlation Coefficient computed between the TRANZ segment from the current response to the segment stored in memory location TRANZ0. Thus, from the 3rd run of the stimuli onwards, with each new run, the bio response is collected, Z+, Z– & TRANZ are identified, CORZ, TRANZT & CORTRAN parameters are calculated and tabulated (block 750). After making enough number of runs with the stimulus, statistically representative values (such as average values) for CORZ, TRANZT & CORTRAN are derived (block 770). A low value of CORZ close to zero (indicating a high surprise factor), a small TRANZT (indicating brevity of after-thoughts) and a high value of CORTRAN close to 1.0 (showing sustenance of the surprise factor in spite of extended use) is sought (block 780) by the subject to accept a certain stimuli as mantra.

If the $1^{st}$ stimulus didn't produce satisfactory results (block 782), runs with the next one is started and previous procedure is repeated.

After selecting the mantra it is optimized (block 790) to enhance its 'dramatic' effects. An example for optimization is adding of a deep silence section (by activating the noise cancelling circuitry of the headset) just before playing of the audio clip. Another example is having a preamble of smell or taste stimuli (subject to the availability of the necessary bio actuators and drivers) just before mantra is played. The process of optimization is very subjective and is done interactively (block 781) with the user. An optimized stimulus is archived (block 790) as a mantra.

Procedure to do Closed-Loop Operation of the Device:

As discussed before, closed loop operation is a process where the subject senses his/her brooding states and develops instincts to flex mind away. Duration of this operation is entirely up to the subject and it may take several months or even years to master the mind flexing skills. FIG. 8 flow-charts the various steps involved in closed loop operation.

After setting the device in the 'Operate Mode', the data acquisition part is adjusted (block 800) so that it is able to collect enough number of samples per channel at the required sampling rate, to compute the AXD attribute (derived per procedure in FIG. 6) every cycle. If AXD attribute chosen is a frequency domain characteristic needing multiple windows & averaging, care needs to be taken to satisfy a maximum of those conditions while remaining within the real time computing power offered by the processor and operating system of the device.

If AXD is detected, it is checked (block 813) whether it lasts longer than 'TL', a first Time Limit prescribed by the subject to weed out short events. This is done by randomly sampling sections of the frame collected, for sustained AXD activity in time or frequency domains. If such activity is found to recur even after 'TL', a running coherence/correlation check is initiated on frames of captured data. Coherence calculation is preferred if multiple windows were involved in the computation of AXD attribute. Correlation coefficient would work better, if dealing with AXDs defined for transient events (such as bursts in EEG, rise in skin conductivity level, temple movements captured by Kome Kami switch etc). If such running coherence (or correlation coefficient) remain above limit 'L1' iteratively set by the user for a second time limit 'TLL' (also set by the user), a mantra alert is played (block 820) to the user.

It may also be noted that the procedure described above to test for sustenance of mental states could also be based on signal attributes not characterized or identified prior to starting the 'Operate Mode'.

Upon receiving the mantra alert, the subject performs (block 830) a 'wake-up act', which comprise of enacting explicit bodily expressions to acknowledge the mantra alert. The wake-up act needs to contain an element of self-reflection and be performed with complete self awareness (not like a mechanical ritual) and positivism. Examples are a wide smile, a deep breath, self-patting on the back or even a few dance steps. These explicit acts break the brooding cycle and instantly switches subject's mind into non-brooding states. In other words, these are optional acts that 'amplify' and 'reinforce' the subject's mantra experience and enhance mantra's power to break ruminating cycles.

As the subject continues wearing and operating the machine he/she learns to tweak its parameters in accordance with mind's sensitivities. For example, there's a chance that none of the brooding events are detected if LI, TL or TLL are set very high. Similarly if the device keeps buzzing mantras too often, it means that it is time to increase the detection threshold values to a comfortable level or check the characteristics of bio signals coming in. After many days (or weeks or even months) of operating the device at a particular setting, it gets to a stage where the subject will be able to 'sense' (as determined and acknowledged by block 840 which monitors trends in brooding durations' consistency against a given threshold setting) the onset of a brooding state and predict a mantra coming, before it is triggered by the device. This happens because of the conditioning of subject's mind on causality between sustenance of the mental state and the stimuli played. In other words, the device becomes able to 'habituate' the subject to the 'togetherness' of a mental state with a stimulus. Block 840 is responsible to validate if the subject is getting 'sufficiently' habituated to the current setting, by analyzing the consistency in subject's past brooding durations. If not, it repeatedly launches block 841 logic until the desirable outcomes prevail consistently. Once the subject gets 'sufficiently' conditioned, it may even be possible for the subject to precipitate a mantra triggering by 'faking' a brooding state. Either way, operating the device becomes an interesting mind game for the subject while he/she sub-consciously learns to watch over or supervise his/her own mental states.

Also at this advanced level, the device' output (i.e. mantra stimuli) can be turned off and yet the subject will be able to 're-enact the mantra experience mentally' (virtual playing of mantra in mind) when events leading to a brooding condition initiates in real life. The mantra, its preamble and the wake-up act integrates into a unique, highly personalized mental experience for the subject which gets embedded in subject's mind. Thus it is enough for the subject to 'mentally replay' the mantra experience to toggle into a non-brooding state.

Explained in blocks 850 and 851 are optional steps where the subject can lower the detection thresholds and get sooner and faster alerts when mind slips into brooding states. This would result in the driving of appropriate hardware challenging the subject to be more sensitive to brooding levels (or challenging to beat the machine unto playing alerts). The ultimate level attainable in this mental game is where the subject's response to a brooding state (which would ideally comprise of self-recollection of the mantra in tandem with self-awakening) becomes near-spontaneous with the brooding state's onset. Thus, such self-awakening traits start manifesting as a natural reflex reaction in the subject's behavior in response to brooding states. As depicted by block 860, the subject wouldn't need to use the machine any more in that level. It may however be noted that said measure of spontaneity is highly subjective and its acceptable levels are best decided by the respective individuals using the device.

To summarize, the activities performed during the operating phase of the device helps the subject develop the supervisory abilities and mental instincts (hence the 'mental muscles') to flex his/her mind at will. Also it leaves the subject with a mantra in the form of an ingrained mental experience that helps him/her easily master mantra meditation techniques such as Transcendental Meditation™

Procedure to do Open-Loop Operation of the Device:

The open loop operation (represented by block 360 of FIG. 3 and elaborated in FIG. 9) is a mode wherein, the subject learns to identify his/her non-brooding (positive) states that usually happens without his/her knowledge. As in the case of closed-loop operation, the device continuously scans (block 910) the EEG stream for a previously determined attribute representing a non-brooding mood. Usually such moods are short transients when compared to the brooding states. As soon as an attribute is detected, the subject is alerted (block 930) using a mantra. When mantra plays, subject takes a moment to reflect (block 940) on his/her state optionally with the help of a ritual. Continuing the open loop operation for several weeks or months, the subject's mind is conditioned on the causality between non-brooding states and mantras.

In the later part of the operation, machine plays (block 950) the same mantra to the subject at random times of the day in an open-loop manner (regardless of input EEG signal state). By virtue of conditioning, subject's mind associates that mantra with non-brooding events. This automatically triggers positive thoughts in subject's mind and helps him/her stay positive.

As in the case of closed loop operation, the mantra and associated personal experiences gets embedded in subject's mind eventually eliminating a need for external stimuli. The subject is able to make use of this mantra when he/she formally initiates mantra meditation.

Description and Operation of Alternative Embodiments—FIG. 10

FIG. 10 depicts a second embodiment of the Mind Strength Trainer that has a 'non-portable' configuration. They are preferably stationed in a controlled environment (such as a physician's office) and hence have the ability to accept and process a slew of bio signal inputs and drive many types of bio actuators than a portable headset device. The subject using such machine will be able to experiment with various bio sensors worn internally or external to the body, tune their gains, acquisition parameters and filter settings to suite personal preferences. Also he/she'll have a chance to evaluate various bio stimuli and tweak their channels before choosing the right one/combination. Thus, this configuration can serve as a test station to study subject's body characteristics and match them with appropriate stimuli. At the same time it may be noted that in a controlled environment, it lacks the ability to monitor or sample 'real life' events that happen in day to day life.

As shown in FIG. 10, signal processing components (1020, 1040) have the same functionalities as the corresponding parts 155,170 and 125 of the $1^{st}$ embodiment, except that they can handle a varied range of inputs and outputs.

Operation of the device remains essentially similar to the first embodiment, except that the user-interface of the software has a more elaborate menu offering more possibilities of mixing and matching signals in accordance with user needs.

CONCLUSIONS, RAMIFICATIONS AND SCOPE

While my above description contains two specificities in hardware configuration of the device, these should not be construed as limitations on the scope, but rather as an exemplification of several embodiments thereof. For example, the device could be built around a handheld device (an iPod for example), sensors & actuators may be wirelessly strewn over the internet or could even be remotely controlled by a physician.

Also it may be noted that Mind Strength Trainer and it's algorithms may be used in less obvious ways as described in FIG. 3. For example, the subject could develop and build on his/her mind flexing abilities even without having or collecting recurring moods (brooding, non-brooding etc), validated libraries of signals or their identified attributes. In such situations the machine will be used to monitor known electrical characteristics (such as the power spectral density of beta component of EEG, computed with 1 Hz bin size, 128 FFT lines, Hanning window, 10 linear averages etc) of the signal and whether they sustain beyond certain duration or not. This or any other method of operation that trains human mind on causality between mental activity and an artificially generated alarm would help attain (mental) supervisory abilities, which is the fundamental building block of any meditation technique.

Also it may be noted that the subject doesn't necessarily need to scientifically derive a mantra as described in specifications. He/she could use commonly or previously known mantras or even use random stimuli (with less desirable effects) to operate the machine.

Further, this machine could be used for different purposes (than as a meditation aid) and by second parties working on subject's mind (than the subject doing it all by himself). For example, it could be used to collect signals while engaged in physical activities of a specific kind. Thus, signals may be collected corresponding to physical conditions such as drowsiness, drunkenness, kicking a ball or running. Or, it could be used by a physician or neuro feedback expert looking for signs of depression etc.

Accordingly, the scope should be determined not by the embodiments illustrated, but by the appended claims and their legal equivalents.

I claim:
1. A system comprising:
a processor,
at least one bio sensor,
at least one bio actuator, and
a memory;
a) wherein said at least one bio sensor is configured to output a bio signal representative of mental states of a user using said system;
b) wherein said at least one bio actuator is configured to impart a bio stimulus alert to said user to cause a shift in the user's mental state, wherein said at least one bio actuator includes at least one of audio, video, smell, taste, and tactile types of stimuli generators;
c) wherein said processor is configured to acquire bio signal samples from said at least one bio sensor, perform computations and output results to said at least one bio actuator in a real-time relationship with said user's mental processes;
d) wherein said memory is configured to store a library of optimized bio stimuli, bio signal attributes (AXD) corresponding to sustaining mental states, and parametric thresholds personalized for said user;
e) wherein said parametric threshold includes, retrievably stored within said memory, a settable short time threshold (TL), a settable long-time threshold (TLL), and a settable magnitude threshold (L1);
f) wherein the processor is configured to identify, the onset of a sustaining mental state of a specific type from other mental states by matching the outputted bio signal attributes against bio signal attributes AXD stored in the memory;
g) wherein the processor is configured to determine if running coherence or correlation attribute exhibited by the outputted bio signal lasts longer than said TL;
h) wherein the processor is configured to determine if running coherence or correlation attribute exhibited by the outputted bio signal lasts longer than said TLL;
i) wherein the processor is configured to determine if magnitude of running coherence or correlation attribute exhibited by the outputted bio signal is larger than said L1;
j) wherein the processor is configured to determine if said sustaining mental state of specific type persists longer than TLL by checking if said running coherence or correlation attribute lasts longer than TLL and if said magnitude of running coherence or correlation attribute remains higher than L1;
k) wherein the processor is configured to terminate said sustaining mental state of specific type by imparting a specific bio stimulus on said user, as soon as said running coherence or correlation attribute is found to persist longer than TLL while said magnitude of running coherence or correlation attribute remains higher than L1, and said specific bio stimulus include at least one of, but not limited to audio, video, smell, taste, and tactile stimuli;

l) wherein the processor is configured to use said specific bio stimulus only if said sustaining mental state to be terminated is of said specific type having said bio signal attribute AXD;

m) wherein the processor is configured to assist the user in determining a level of consistency in the measured sustenance durations among recurring occurrences of said specific sustaining mental state, under the control of said specific bio stimulus, and under a chosen setting of L1 and TLL;

n) wherein the processor is configured to assist said user in improving said level of consistency by allowing the user adjusting L1 and TLL; and o) wherein said processor is configured to subject said user to identical mental episodes having identical bio signal attributes AXD, identical durations TLL and identical termination alerts, on a plurality of occasions, until said user's mind getting conditioned to said mental episodes, resulting in self alerts happening ahead of an elapse of TLL, and at the level of consistency desired by said user.

2. System of claim 1 wherein said bio signal is combinatorially derived from a plurality of said bio sensors of similar or dissimilar types whose outputs are converted into electrical domain for processing.

3. System of claim 1 wherein said bio stimulus is combinatorially derived from a plurality of said bio actuators of similar or dissimilar types.

4. A method of using at least a processor, a bio sensor, and a bio actuator to alert a subject causing a shift in a specific sustaining mental state of said subject comprising:

a) a first step of continuously receiving at least one bio signal indicative of mental processes of said subject in a processor;

b) a second step of determining in the processor if said bio signals manifest an attribute indicative of said specific sustaining mental state;

c) a third step of measuring persistence of said specific sustaining mental state by continuously calculating in the processor, a running coherence or correlation attribute of said bio signal;

d) a fourth step of terminating said specific sustaining mental state using said bio actuator to impart stimuli not limited to audio, video, smell, taste, tactile and an optimal type, on said subject if said measured persistence is larger than a level threshold L1 and a lasts longer than a duration threshold TLL;

e) repeating by the processor said second, third and fourth steps on said subject on a real-time relationship with user's mental processes, each time said user slips into said specific sustaining mental state;

f) determining in the processor, a level of consistency in the measured sustaining mental state durations among past occurrences of said specific sustaining mental state, while under the control of said specific bio stimuli, and under chosen settings for L1 and TLL;

g) guiding interactively by the processor to adjust L1 and TLL enabling the user improve said level of consistency; and h) building said subject's ability to self-alert from said specific sustaining mental states before an elapse of TLL, thereby enabling said subject to self-administer highly effective bio feedback therapy utilizing own brooding habits.

5. Method of claim 4 wherein said specific sustaining mental state is validated using steps comprising:

a) self-marking and archiving of a segment of said bio signal pertaining to said sustaining mental state at a plurality of occasions by said user; and b) finding mathematical attributes common to the archived segments that help identify said specific sustaining mental state.

6. Method of claim 4 wherein said optimized stimulus is derived from at least a first member stimulus from a group of stimuli by adding a prelude of altered stimulus to an un-altered stimulus, including but not limited to adding an actively noise canceled, deep silence period in the beginning of an audio stimulus.

* * * * *

UNITED STATES PATENT AND TRADEMARK OFFICE
CERTIFICATE OF CORRECTION

PATENT NO. : 11,471,091 B2  
APPLICATION NO. : 12/931101  
DATED : October 18, 2022  
INVENTOR(S) : Kulangara Sivadas Page 1 of 2

It is certified that error appears in the above-identified patent and that said Letters Patent is hereby corrected as shown below:

In the Claims

Column 16, Line 33, Claim 1, change "threshold includes" to read as --thresholds include--;
    Line 38, Claim 1, change "the" to read as --an--;
    Line 40, Claim 1, change "matching the outputted" to read as --matching outputted--.

Column 17, Lines 6-7, Claim 1, delete "the measured substance durations among--;
    Line 8, Claim 1, change "the control" to read --control--;
    Line 13, Claim 1, change "adjusting" to read --to adjust--;
    Line 17, Claim 1, change "mind getting" to read as --mind is getting--.

Column 17, Line 22, Claim 2, change "said bio sensors" to read as --said at least one bio sensor--.

Column 17, Line 26, Claim 3, change "said bio actuators" to read as --said at least one bio actuator--.

Column 17, Lines 32-33, Claim 4, change "in a processor" to read as --in the processor from said bio sensor--;
    Line 34-35, Claim 4, change "if said bio signals manifest" to read as --that said at least one bio signal manifests--;
    Line 40, Claim 4, change "said bio" to read as --said at least one bio--.

Column 18, Line 3, Claim 4, before "not" insert --including at least one of but--;
    Line 3-4, Claim 4, change "tactile and an optimal type," to read as --and tactile types,--;
    Line 5, Claim 4, change "larger than a level" to read as --larger than a magnitude level--;
    Line 8-9, Claim 4, change "with user's" to read as --with subject's--;
    Line 9, Claim 4, change "said user" to read as --said subject--;
    Line 11, Claim 4, change "determining in" to read as --determining, with assistance from--;
    Line 12, Claim 4, change "the measured sustaining mental state durations among past occurrences" to read as --recurring occurrences--;
    Line 14, Claim 4, change "the control of said specific bio" to read as --control of said--;

Signed and Sealed this  
Fourth Day of July, 2023

Katherine Kelly Vidal  
*Director of the United States Patent and Trademark Office*

CERTIFICATE OF CORRECTION (continued)
U.S. Pat. No. 11,471,091 B2

Line 17, Claim 4, change "guiding interactively by the processor, to adjust" to read as --adjusting, with assistance from the processor,--;
Line 18, Claim 4, change "the user improve" to read as --the subject to improve--;
Line 21, Claim 4, change "mental states" to read as --mental state--.

Column 18, Line 27, Claim 5, change "said bio" to read as --said at least one bio--; and
Line 29, Claim 5, change "said user" to read as --said subject--.

Column 18, Line 33, Claim 6, change "said optimized stimulus is" to read as --said stimuli is an optimized stimulus--;
Line 37, Claim 6, change "the" to read as --a--.